United States Patent [19]

Aoki et al.

[11] Patent Number: 4,638,050
[45] Date of Patent: Jan. 20, 1987

[54] THROMBIN-BINDING SUBSTANCE AND PROCESS FOR ITS PRODUCTION

[75] Inventors: Nobuo Aoki, Tokyo, Japan; Shinichiro Kurosawa, Oklahoma City, Okla.

[73] Assignee: Kowa Co., Ltd., Nagoya, Japan

[21] Appl. No.: 713,821

[22] Filed: Mar. 20, 1985

[30] Foreign Application Priority Data

Mar. 23, 1984 [JP] Japan ................................. 59-55792

[51] Int. Cl.[4] ........................... C07K 3/20; C07K 3/28
[52] U.S. Cl. ................................... 530/413; 424/105; 424/101; 530/350; 530/399; 530/851
[58] Field of Search ............................... 424/105, 101; 260/112 R

[56] References Cited

U.S. PATENT DOCUMENTS 4,269,825  5/1981  Bohn et al. ............................ 424/85
4,301,064  11/1981 Bohn ................................ 260/112 R
4,379,142  5/1983  Port et al. ........................... 424/101

OTHER PUBLICATIONS

J. Biological Chemistry, 257, 859–864 (1982), Esmon et al.

Primary Examiner—Howard E. Schain
Attorney, Agent, or Firm—Oblon, Fisher, Spivak, McClelland & Maier

[57] ABSTRACT

A thrombin-binding substance derived from human tissue and having the characteristics of (a) molecular weight: 88,000±20,000 in reduced condition and 71,000±20,000 in unreduced condition; (b) isoelectric point: $pH$ 4.2±0.5; (c) affinity: strong for thrombin; (d) activities: capable of promoting the thrombin-catalyzed activation of protein C and prolonging clotting time; and (e) stability: stable over a $pH$ range of 2 to 10 and stable to denaturing agents (sodium dodecylsulfate and urea) and to a pepsin treatment, is effectively useful for thrombolysis and anticoagulation.

5 Claims, 4 Drawing Figures

THROMBIN-BINDING SUBSTANCE AND PROCESS FOR ITS PRODUCTION

BACKGROUND OF THE INVENTION

1. Field of the Invention

This invention relates to a novel thrombin-binding substance and a process for producing such substance.

2. Description of the Prior Art

A variety of researches have heretofore been conducted into the role which thrombin plays as a proteolytic enzyme in the control mechanism of blood coagulation, whereby the mechanism of the coagulation system has been substantially fully elucidated. Recently, it has been reported by N. L. Esmon et al that thrombin serves to activate protein C in a living body, which protein C is said to act on the fibrinolysis and anticoagulation mechanisms, and that a factor capable of functioning as a coenzyme for such activation system is present in extracts of rabbit lung tissue [J. Biological Chemistry, 257, 859–864 (1982)].

The present inventors have directed their extensive studies to the role of thrombin in the human coagulation and fibrinolysis mechanisms, especially to the effect of thrombin on the fibrinolysis mechanism. It has now been found that thrombin takes part in the activation of protein C even in human blood vessels and that a factor exists which, when bonded with thrombin, can accelerate the activation of protein C. It has also been found that such factor can be isolated in pure form from human placentae.

SUMMARY OF THE INVENTION

It is one object of this invention to provide a novel thrombin-binding substance which is derived from human tissue and which is effectively useful as a thrombolytic agent or an anticoagulating agent in that, when bonded with thrombin, the substance specifically enhances the activation of protein C and hence prolongs clotting time.

Another object of the invention is to provide a process for producing the thrombin-binding substance.

According to the invention, there is provided a thrombin-binding substance derived from human tissue and having the characteristics of:

(a) molecular weight: 88,000±20,000 in reduced condition and 71,000±20,000 in unreduced condition;
(b) isoelectric point: $_p$H 4.2±0.5;
(c) affinity: strong for thrombin;
(d) activities: capable of promoting the thrombin-catalyzed activation of protein C and prolonging clotting time; and
(e) stability: stable over a $_p$H range of 2 to 10 and stable to denaturing agents (sodium dodecylsulfate and urea) and to a pepsin treatment.

According to the invention, there is also provided a process for producing a thrombin-binding substance derived from human tissue and having the characteristics of:

(a) molecular weight: 88,000±20,000 in reduced condition and 71,000±20,000 in unreduced condition;
(b) isoelectric point: pH 4.2±0.5;
(c) affinity: strong for thrombin;
(d) activities: capable of promoting the thrombin-catalyzed activation of protein C and prolonging clotting time; and
(e) stability: stable over a $_p$H range of 2 to 10 and stable to denaturing agents (sodium dodecylsulfate and urea) and to a pepsin treatment, which comprises the steps of:

(a) extracting fragments of a human placenta with a buffer containing a non-ionic surfactant; and
(b) isolating said thrombin-binding substance in pure form from the resulting extract by means of diisopropylphosphoro-thrombin affinity chromatography, gel filtration or a combination thereof.

BRIEF DESCRIPTION OF THE DRAWINGS

A fuller understanding of this invention will be had from the following detailed description when considered in connection with the accompanying drawings, wherein.

DETAILED DESCRIPTION OF THE INVENTION

A thrombin-binding substance according to this invention can be produced for example by extracting fragments of a human placenta with a buffer containing a non-ionic surfactant, and then isolating the thrombin-binding substance in pure form from the resulting extract by means of diisopropylphosphoro-thrombin (hereinafter referred to simply as "DIP-thrombin") affinity chromatography and/or gel filtration.

More particularly, a human placenta is washed with a tris-HCl buffer containing sucorse and benzamidine hydrochloride or with an analogous solution and then ground into a homogeneous mixture. The resulting mixture is centrifuged or treated in like manner to collect a precipitate. The precipitate is extracted with a solution which has been obtained by adding Triton X-100, Lubrol PX or the like to the buffer referred to above (Triton X-100 and Lubrol PX are the products of Sigma Corporation). Thereafter, the extract is caused to pass through a DIP-thrombin affinity chromatographic column packed with a carrier such as DIP-thrombin-agarose or the like to thereby allow active fractions to be adsorbed in the column. Upon elution of the column with a tris-HCl buffer containing sodium chloride, EDTA, benzamidine hydrochloride and Triton X-100, the substance contemplated by the invention is obtainable.

Alternatively, gel filtration may be suitably employed to collect those active fractions. Where it is found desirable, both of the affinity chromatography and gel filtration techniques may be used in combination.

The thrombin-binding substance of the invention has the following characteristics.

(a)

Molecular Weight:
88,000±20,000 in reduced condition
71,000±20,000 in unreduced condition
Measurement Method:

In accordance with Laemmli's method [Nature, 227, 680–685 (1970)], measurement was made by electrophoresis using a 7.5% sodium dodecylsulfate (SDS) polyacrylamide. As a standard protein, there was used Bio-Rad SDS-PAGE Standard (for high-molecular proteins; product of Nippon Bio-Rad Laboratories, K. K.). Reduction was effected by treating the thrombin-binding substance with 2% dithiothreitol at 100° C. for 3 minutes.

(b)

Isoelectric Point:
pH 4.2±0.5

Isoelectric fractions were measured by isoelectric electrophoresis using an ampholyte.

(c)

Affinity:
The thrombin-binding substance has strong affinity for thrombin. It adsorbed approximately 100% of thrombin in a chromatographic treatment using DIP-thrombin-agarose [J. Biological Chemistry, 245, 3059–3065 (1970)].

(d)

Activities:
(1) The thrombin-binding substance acts as a cofactor for the thrombin-catalyzed activation of protein C.

Figure 1:
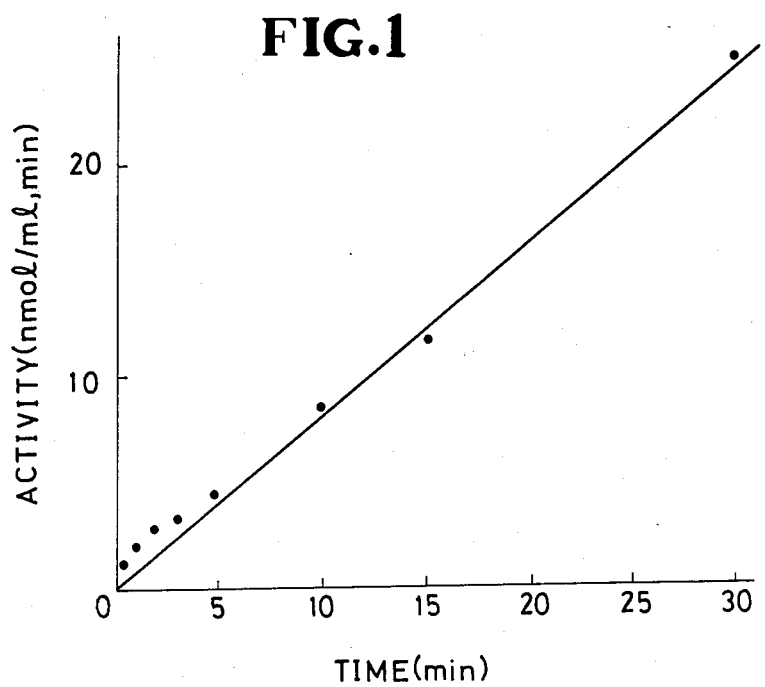
FIGS. 1 and 2 are diagrams each illustrating the promoting effect of a thrombin-binding substance of the invention on the thrombin-catalyzed activation of protein C.

Measurement Method 1:
In 40 $\mu$l of a 0.02M tris-HCl buffer ($_p$H 7.5) containing 0.1M sodium chloride and 3.5 mM calcium chloride were dissolved 5 $\mu$l of protein C (7.32 $\mu$M), 5 $\mu$l of a solution containing the substance of the invention (0.055 $A_{280}$/ml) and 50 $\mu$l of thrombin (4 U/ml). The resulting solution was incubated at 37° C. for 0 to 30 minutes. After addition of 150 $\mu$l of anti-thrombin III (16.1 $\mu$M), the mixture was incubated at 37° C. for 15 minutes, whereupon the reaction was terminated. To the reaction mixture was added 250 $\mu$l of a buffer solution containing 100 $\mu$M of Boc-Leu-Ser-Thr-Arg-MCA (product of Protein Research Foundation, Osaka, Japan). After reaction of the resulting mixture at 37° C. for 10 minutes, 500 $\mu$l of 20% acetic acid was added to terminate the reaction. The concentration of liberated AMC was measured at an excitation wavelength of 380 nm and an emission wavelength of 460 nm by means of a spectrofluorometer, from which the concentration of activated protein C was determined. The results are shown in FIG. 1.

Figure 2:
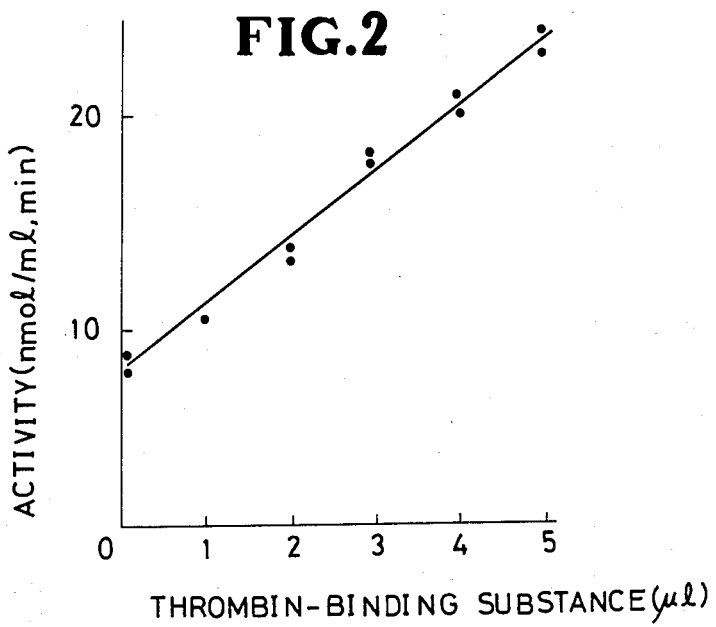

Measurement Method 2:
In 40 $\mu$l of a 0.02M tris-HCl buffer ($_p$H 7.5) containing 0.1M sodium chloride and 3.5 mM calcium chloride were dissolved 5 $\mu$l of protein C (7.32 $\mu$l), 0 to 5 $\mu$l of the substance of the invention (0.055 $A_{280}$/ml), 5 to 0 $\mu$l of a 0.02M tris-HCl buffer ($_p$H 7.5) which contained 0.1M sodium chloride and 0.5% Lubrol PX, and 50 $\mu$l of thrombin (4 U/ml). The resulting solution was incubated at 37° C. for 30 minutes. After addition of 150 $\mu$l of anti-thrombin III, the mixture was incubated at 37° C. for 15 minutes to terminate the reaction. In the same manner as in Measurement Method 1, the concentration of liberated AMC was measured using an MCA substrate. The results are shown in FIG. 2.

It is to be noted from these results that the thrombin-binding substance of the invention promotes the thrombin-catalyzed activation of protein C.

(2) The thrombin-binding substance prolongs clotting time.

Measurement Method (activated partial thromboplastin time):
A solution of the substance of the invention (0.055 $A_{280}$/ml) was poured in portions (0, 2.5, 5.0 and 10.0 $\mu$l) into fibrocups. Each of the fibrocups was added with 0.1 ml of kaolin-added and activated cephaloplastin ("Actin"; product of Dade Diagnostic Inc.), followed by heating to 37° C. One minute later, the fibrocup was added with 0.1 ml of platelet-poor plasma which had been added with sodium citrate and heated to 37° C. Thereafter, a fibrometer (made by Becton-Dickinson Company) was actuated to measure the clotting time. The results are shown in the Table below.

TABLE

| Samples ($\mu$l) | Clotting time (sec) | |
|---|---|---|
| | Test | Control |
| 0 | | 26.1 |
| 2.5 | 68.4 | 30.4 |
| 5.0 | 103.9 | 32.9 |
| 10.0 | 200 | 37.3 |

It is to be noted from these results that the thrombin-binding substance of the invention has an anticoagulating effect on blood and hence prolongs the clotting time as the concentration of the substance increases.

(e)

Stability:

| Conditions | Residual activity |
|---|---|
| Reduction treatment with 1% $\beta$-mercaptoethanol | 29% |
| Denaturing agents | |
| 1% SDS | 92% |
| 8 M Urea | 100% |
| 6 M Guanidium chloride | 77% |
| $_p$H 2 | 95% |
| $_p$H 10 | 99% |
| Pepsin treatment | 89% |
| Heat treatment | 20 min. |

Measurement Method:
The substance of the invention (0.073 $A_{280}$/ml) was treated at 25° C. for 150 minutes under each of the conditions as listed above. After completion of the treatment, the resulting mixture was diluted 100 times with tris-buffered saline and measured with respect to its activity. From the activity level of an untreated sample, the residual activity was calculated. Pepsin was used in such an amount that the final concentration and $_p$H reached 2.5 g/ml and $_p$H 2.5, respectively. The pepsin treatment was performed at 37° C. for 2 hours. The heat treatment was conducted at 100° C. and at $_p$H 7.5. The residual activity is expressed in terms of half time.

The following example is given to further illustrate this invention, but it is to be understood that the invention is not limited thereto.

EXAMPLE (1) About 1.0 kg of a human placenta (equivalent to two placentae) was washed with a 0.02M tris-HCl buffer ($_p$H 7.5) containing 0.25M sucrose and 1 mM of benzamidine hydrochloride and then ground into a homogeneous liquid mixture. The homogenized mixture was centrifuged at 30,000 G for 40 minutes to collect a precipitate. The precipitate was suspended in the buffer just mentioned above and again centrifuged to collect a precipitate. The above procedure was repeated five times. The precipitates collected were combined together and extracted with 300 ml of a 0.02M tris-HCl buffer ($_p$H 7.5) containing 0.25M sucrose, 1 mM of benzamidine hydrochloride and 0.5% (v/v) Triton X-100 to thereby obtain a crude extract. The protein concentration of the crude extract (315 ml) was 1.17 $A_{280}$/ml. The crude extract (315 ml) was then subjected to a DIP-thrombin-agarose column which had been equilibrated with a 0.02M tris-HCl buffer ($_p$H 7.5) containing 0.1M sodium chloride, 0.5 mM calcium chloride, 0.1 mM benzamidine hydrochloride and 0.5% (v/v) Triton X-100. The column was then washed with 1,500 ml of the buffer which had been used for the equilibration. The washings were collected in 16.7 ml-fractions by means of a fraction collector.

Figure 3:
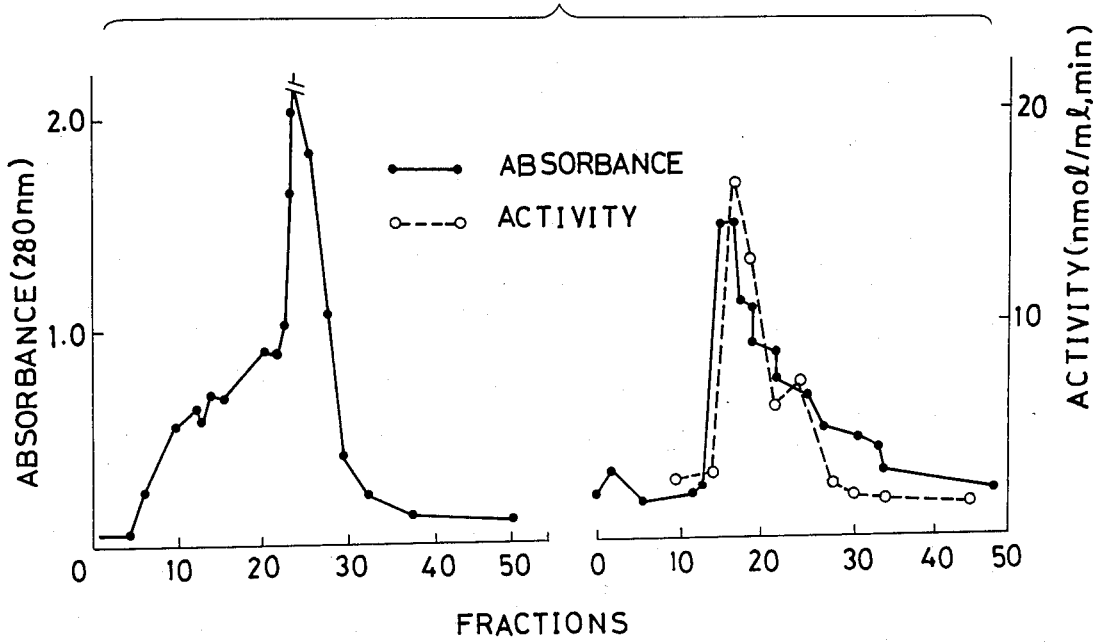
FIG. 3 is a diagram illustrating the elution pattern obtained by subjecting a human placental extract to affinity chromatography.

The column was then eluted using as an eluant 350 ml of a 0.02M tris-HCl buffer ($_p$H 7.5) containing 1M of sodium chloride, 0.1 mM of EDTA, 1 mM of benzamidine hydrochloride and 0.5% (v/v) Triton X-100. The protein concentrations and activity levels of the washings and eluate were respectively measured. The results are shown in FIG. 3.

The protein concentrations were measured in accordance with Lowry's method, while the activity levels were measured by the method set forth under Measurement Method 1 of paragraph (d) above.

(2) The 16th to 29th fractions (94 ml in total) of the eluate were dialyzed against the buffer solution which had been used to equilibrate the column, thereby obtaining a solution (103 ml). The solution was subjected to a DIP-thrombin-agarose column which had been treated in the same manner as in item (1) of this Example.

Thereafter, the column was washed with 10 ml of a 0.02M tris-HCl buffer ($_p$H 7.5) containing 0.4M sodium chloride, 0.5 mM of calcium chloride, 0.1 mM of benzamidine hydrochloride and 0.5% of Triton X-100, and then with 10 ml of a buffer ($_p$H 7.5) having the same composition as the buffer just mentioned except for the use of 1 mM of EDTA in place of calcium chloride.

Figure 4:
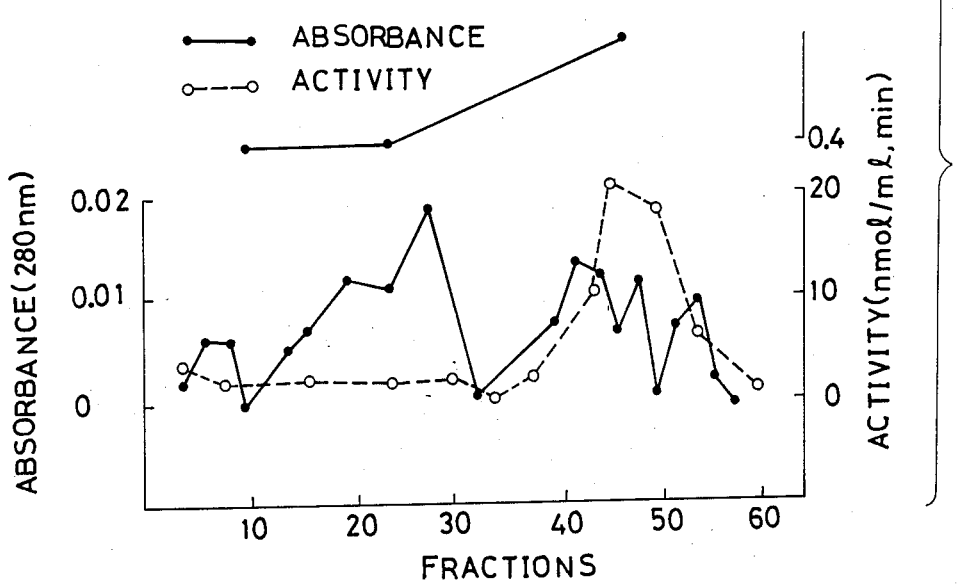
FIG. 4 is a diagram illustrating the elution pattern obtained by subjecting the 16th to 29th fractions of the extract of FIG. 3 to affinity chromatography.

Using as an eluant 100 ml of a solution obtained by adding sodium chloride (0.4M to 1M) to a 0.02M tris-HCl buffer ($_p$H 7.5) which contained 0.1 mM of EDTA, 1 mM of benzamidine hydrochloride and 0.5% Triton X-100, the column was eluted by a gradient elution technique. The eluate was collected in 4.4 ml-fractions. The protein concentration and activity level of the eluate were measured in the same manner as in item (1) above. The results are shown in FIG. 4.

The 38th to 57th eluate fractions were collected to obtain 88 ml of the thrombin-binding substance of the invention, the protein concentration of which was 0.057 $A_{280}$/ml.

Having thus described this invention, it will be apparent to those versed in the art that various changes and modifications may be made thereto without departing from the scope or spirit of the invention set out in the appended claims.

What is claimed is:

1. A thrombin-binding substance derived from human tissue and obtained by (1) extracting human tissue with a buffer containing a non-ionic surfactant, and (2) isolating the said thrombin-binding substance in pure form from the resulting extract by diisopropylphosphorothrombin affinity chromatography, gel filtration, or a combination thereof; said thrombin-binding substance having the following properties:
    (a) molecular weight: 88,000±20,000 in reduced form, and 71,000±20,000 in unreduced form;
    (b) isoelectric point: pH 4.2±0.5;
    (c) affinity: strong for thrombin;
    (d) activity: capable of promoting the thrombin-catalyzed activation of protein C and prolonging clotting time; and
    (e) stability: stable over a pH range of 2 to 10 and stable to denaturing agents and to a pepsin treatment.

2. The thrombin-binding substance of claim 1, wherein the said denaturing agents comprise sodium dodecylsulfate and urea.

3. A process for producing a thrombin-binding substance derived from human placenta and having the following properties:
    (a) molecular weight: 88,000±20,000 in reduced form, and 71,000±20,000 in unreduced form;
    (b) isoelectric point: pH 4.2±0.5;
    (c) affinity: strong for thrombin;
    (d) activity: capable of promoting the thrombin-catalyzed activation of protein C and prolonging clotting time; and
    (e) stability: stable over a pH range of 2 to 10 and stable to denaturing agents (sodium dodecylsulfate and urea) and to a pepsin treatment,
said process comprising the steps of:
    (1) washing human placenta with tris-HCL buffer containing sucrose and benzamidine hydrochloride,
    (2) grounding the human placenta into a homogeneous mixture,
    (3) treating the mixture to collect a precipitate,
    (4) extracting the precipitate with a buffer solution containing a nonionic surface-active agent,
    (5) isolating the extract, and
    (6) eluting the isolated substance with a tris-HCL buffer solution containing sodium chloride, ethylenediaminetetraacetic acid, benzamidine hydrochloride and a nonionic surface-active agent.

4. The process of claim 3, wherein the said treating step (3) comprises centrifuging.

5. The process of claim 3, wherein the said isolating step (5) is achieved by diisopropylphophorothrombin affinity chromatography, gel filtration, or a combination thereof.

* * * * *